United States Patent [19]

Bokerman et al.

[11] Patent Number: 5,175,329
[45] Date of Patent: Dec. 29, 1992

[54] PRODUCTION OF ORGANOSILANES FROM POLYSILANES

[75] Inventors: Gary N. Bokerman, Midland, Mich.; John P. Cannady, Madison, Ind.; Ann E. Ogilvy, Eugene, Oreg.

[73] Assignee: Dow Corning Corporation, Midland, Mich.

[21] Appl. No.: 862,856

[22] Filed: Apr. 3, 1992

[51] Int. Cl.⁵ .................................................. C07F 7/08
[52] U.S. Cl. .................................................. 556/467
[58] Field of Search ........................................ 556/467

[56] References Cited

U.S. PATENT DOCUMENTS

| | | | |
|---|---|---|---|
| 2,380,995 | 8/1945 | Rochow | 260/607 |
| 2,488,487 | 11/1949 | Barry et al. | 260/448.2 |
| 2,598,435 | 5/1952 | Mohler et al. | 260/448.2 |
| 2,606,811 | 8/1952 | Wagner | 23/14 |
| 2,681,355 | 6/1954 | Barry et al. | 260/448.2 |
| 3,099,671 | 7/1963 | George | 556/467 |
| 3,639,105 | 2/1972 | Atwell et al. | 23/366 |
| 4,079,071 | 3/1978 | Neale | 260/448.2 |
| 4,393,229 | 7/1983 | Ritzer et al. | 556/430 |
| 4,958,040 | 9/1990 | Yoshioka et al. | 556/467 |

OTHER PUBLICATIONS

Lewis, Selective Hydrogenolysis of Methylchlorodisilanes using Rhenium-Containing Catalysts. At Preliminary Abstract Inorganic Presentation No. 52, ACS Meeting, San Francisco, Calif., Apr. 5, 1992.

Primary Examiner—Paul F. Shaver
Attorney, Agent, or Firm—William F. Boley

[57] ABSTRACT

The present invention is a process for the production of organosilanes from the high-boiling residue resulting from the reaction of organohalides with silicon metalloid in a process typically referred to as the "direct process." The present process comprises forming a mixture comprising a organotrihalosilane and the high-boiling residue in the presence of hydrogen gas, a hydrogenolysis catalyst, and a redistribution catalyst. The organotrihalosilane and high-boiling residue are converted into commercially useful di- and triorganosilanes and organohydrosilanes. The present process results in consumption of the organotrihalosilane rather than the net increase which typically occurs in the absence of the redistribution catalyst.

27 Claims, No Drawings

PRODUCTION OF ORGANOSILANES FROM POLYSILANES

BACKGROUND OF INVENTION

The present invention is a process for the production of organosilanes from the high-boiling residue resulting from the reaction of organohalides with silicon metalloid in a process typically referred to as the "direct process". The present process comprises forming a mixture comprising an organotrihalosilane and the high-boiling residue in the presence of hydrogen gas, a hydrogenolysis catalyst, and a redistribution catalyst. The organotrihalosilane and high-boiling residue are converted into commercially useful organosilanes particularly di- and triorganohalosilanes and organohydrosilanes. The present process results in consumption of the organotrihalosilane rather than a net increase which typically occurs upon hydrogenolysis of the residue in the absence of the redistribution catalyst.

In the preparation of organohalosilanes, various polysilane products are formed during the reaction and remain in the residue after the separation of the monosilanes. For example, in the commercial method known as the "direct process," in addition to the monosilanes, which in the case of the chloromonosilanes include dimethyldichlorosilane, methyltrichlorosilane, and trimethylchlorosilane there is always obtained a variety of compounds which boil above the monosilanes, that is above about 70° C., which is hereafter referred to as "high-boiling residue." The "direct process" is well described in the patent literature, for example, in Rochow, U.S. Pat. No. 2,380,995, issued Aug. 7, 1945 and Barry et al., U.S. Pat. No. 2,488,487, issued Nov. 15, 1949. The residue after removing the monosilanes is a complex mixture of compounds that include SiSi, SiOSi, and SiCSi linkages in the molecules. Typical residues are described in Mohler et al., U.S. Pat. No. 2,598,435, issued May 27, 1952 and Barry et al., U.S. Pat. No. 2,681,355, issued Jun. 15, 1954.

In current commercial operations for performing the direct process, the high boiling residue can constitute as much as five percent of the resultant product. Therefore, it is desirable to convert the high-boiling residue into commercially desirable products to both reduce waste disposal and to improve raw material utilization.

Wagner, U.S. Pat. No. 2,606,811, issued Aug. 12, 1952, teaches a hydrogenolysis process where a compound containing a halogen and the Si—Si bond is heated to a temperature of at least about 300° C. in the presence of hydrogen. The resultant products are monosilanes.

Atwell et al., U.S. Pat. No. 3,639,105, issued Feb. 1, 1972, describes a process where hydrosilanes are produced by contacting a disilane with hydrogen gas under pressure and heating the mixture in the presence of a transition metal catalyst such as palladium on charcoal. When the disilane was a methylchlorodisilane, the resulting product contained about four to 28 weight percent of methyltrichlorosilane. Generally, organotrihalosilanes such as methyltrichlorosilane have limited commercial usefulness and for this reason limit the usefulness of the process described by Atwell et al.

Neale, U.S. Pat. No. 4,079,071, issued Mar. 14, 1978, describes a process for preparing high yields of hydrosilanes by reacting methylchloropolysilanes with hydrogen gas under pressure at a temperature of from about 25° C. to about 350° C. in the presence of a copper catalyst. Useful copper catalysts described by neale include copper metal, copper salts, and complexes of copper salts with organic ligands. Neale reports an experiment in which the level of methyltrichlorosilane was elevated to about 12 weight percent of a disilane mixture. This mixture, containing the elevated level of methyltrichlorosilane, was contacted with hydrogen gas and a raney nickel catalyst for one hour at 350° C. Neale concluded that no substantial change in product distribution occurred particularly in regard to the level of methyltrichlorosilane.

Therefore, in view of Neale and of Atwell et al., unexpectedly the inventors have discovered a process in which the addition of organotrihalosilane to the process results in a net consumption of the organotrihalosilane, as opposed to the production of organotrihalosilane as previously reported.

Ritzer et al., U.S. Pat. No. 4,393,229, issued Jul. 12, 1983, describes a process for converting the alkyl-rich disilanes in the residue obtained from the manufacture of alkylhalosilanes to halogen-rich polysilanes with alkyltrihalosilanes. The process simultaneously converts the alkyltrihalosilanes to dialkyldihalosilanes by reacting the alkyl-rich polysilanes in the residue and the alkyltrihalosilanes at an elevated temperature in the presence of a suitable catalyst and a catalytic amount of a hydrosilane reaction promoter. Ritzer et al. reported a preferred embodiment to be treating the residue containing alkyl-rich disilanes with methyltrichlorosilane at a temperature of about 100° C. to about 250° C. in the presence of aluminum trichloride and a catalytic amount of methyldichlorosilane. Although Ritzer et al. report the use of the redistribution catalyst, aluminum chloride, to effect a redistribution between disilanes and an organotrihalosilane, they do not recognize that this reaction can be combined with a hydrogenolysis process to achieve the beneficial results described herein.

The object of the present invention is to provide a process where the high-boiling residue from a direct process for producing organosilanes can be converted into commercially useful organosilanes while resulting in a net consumption of organotrihalosilanes.

SUMMARY OF INVENTION

The present invention is a process for the production of organosilanes from the high boiling residue resulting from the reaction of organohalides with silicon metalloid in a process typically referred to as the "direct process". The present process comprises forming a mixture comprising a organotrihalosilane and the high-boiling residue in the presence of hydrogen gas, a hydrogenolysis catalyst, and a redistribution catalyst The organotrihalosilane and high-boiling residue are converted into commercially useful di- and triorganosilanes and organohydrosilanes. The present process results in consumption of the organotrihalosilane rather than the net increase which typically occurs in the absence of the redistribution catalyst

DESCRIPTION OF INVENTION

The present invention is a process for converting polysilanes to organosilanes and in the process consuming organotrihalosilane. The process comprises:
(A) forming a mixture comprising a high boiling residue comprising polysilanes of formula

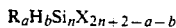

$$R_aH_bSi_nX_{2n+2-a-b} \qquad (1)$$

and an organotrihalosilane of formula $$RSiX_3 \quad (2)$$

(B) contacting the mixture with hydrogen gas at a pressure of 50 psig to 10,000 psig a hydrogenolysis catalyst, and a redistribution catalyst, at a temperature of 100° C. to 400° C. and (C) recovering organosilanes of formula $$R_cH_dSiX_{4-c-d} \quad (3)$$

where each R is a radical independently selected from a group consisting of alkyls of one to six carbon atoms, aryls, alkoxys of one to six carbon atoms, trimethylsilyl, and trifluoropropyl X is a halogen n=2 to 20, a=0 to 2n+2, b=0 to 2n+2, a+b=0 to 2n+2, c=1, 2, 3, or 4, d=0, 1, or 2, and c+d=2, 3, or 4.

The present process may be run in any standard high pressure reactor. The process may be run as a batch process for example in stirred reactor, a stirred-bed reactor, or a fixed-bed reactor. The process may be run as a continuous process in, for example, a high-pressure coil reactor.

The present process is useful for converting a high-boiling residue comprising polysilanes described by Formula (1) into organosilanes as described by Formula (3). The term "high-boiling residue" refers to those materials with a boiling point above about 70° C. which result from the reaction of an organohalide with silicon metalloid. In a typical process for reacting an organohalide with silicon metalloid, the process is conducted at a temperature of about 300° C. to 350° C. in the presence of a suitable catalyst, and gaseous product and feed are continuously removed from the process. The removed gaseous products and feed are subsequently distilled to remove organohalosilanes leaving a high-boiling residue comprising a significant fraction of polysilanes. The polysilanes present in the high-boiling residue can consist of n number of silicon atoms where n is an integer from two to 20. Preferred is when n equals two. The polysilanes are substituted with a number of R radicals, where a=0 to 2n+2 and each R is selected from a group consisting of alkyls of one to six carbon atoms aryls alkoxys of one to six carbon atoms, trimethylsilyl, and trifluoropropyl. Preferred is when the polysilanes are substituted with (2n+2)/2 to 2n+2 of the R radicals. The radical R can be, for example, methyl, ethyl, propyl, t-butyl, benzyl, xylyl, methoxy, and phenoxy. Preferred is when R is methyl.

The polysilanes in the high-boiling residue can contain b number of hydrogen atoms substituted on the silicon atoms, where b=0 to 2n+2.

The polysilanes in the high-boiling residue can contain from zero to 2n+2 substituents, X, where X is a halogen selected from a group consisting of bromine, chlorine, iodine, and fluorine. The preferred halogen is chlorine.

Those skilled in the art will recognize that the high-boiling residue in addition to polysilanes may contain other high boiling materials such as disilmethylenes all of which may be involved in the hydrogenolysis and redistribution reactions of the present process.

The preferred high-boiling residue for use in the present process has a boiling point greater than about 70° C. and results from the reaction of methyl chloride with silicon metalloid. The polysilanes present in this high-boiling residue can be disilanes, for example, $Me_2ClSiSiClMe_2$, $Me_2ClSiSiCl_2Me$, and $MeCl_2SiSiCl_2Me$.

As previously discussed, the high boiling residue can be treated with a hydrogenolysis catalyst and hydrogen gas to produce monosilanes. However, a consequence of this hydrogenolysis process is the production of organotrihalosilanes which have limited commercial utility and therefore are an undesired product. The inventors have unexpectedly found that by running the hydrogenolysis process in the presence of both a hydrogenolysis catalyst and a redistribution catalyst and added organotrihalosilane the organotrihalosilane is consumed in the process.

Therefore, a mixture of the high-boiling residue is formed with an organotrihalosilane as described by Formula (2). The mixture can be formed external to the reactor and added to the reactor or be formed by adding the individual components to the reactor. The organotrihalosilane contains one substituent R, where R is as previously described. Preferred is where R is methyl. The organotrihalosilane contains three halogen substituents, X, where X is as previously described. Preferred is when X is chlorine. The organotrihalosilane can be, for example, methyltrichlorosilane, ethyltrichlorosilane, benzyltrichlorosilane, methyltribromosilane, methyltriiodosilane, and methyltrifluorosilane. Preferred is when the organotrihalosilane is methyltrichlorosilane.

The weight percent of organotrihalosilane in the mixture with the high-boiling residue is not critical to the present process. Generally, a mixture where the organotrihalosilane is about 0.1 to 60 weight percent of the mixture is considered useful. Preferred is where the organotrihalosilane is about 30 to 50 weight percent of the mixture.

The mixture is contacted with hydrogen gas at a pressure of about 50 psig to 10,000 psig. Preferred is a hydrogen gas pressure of about 500 psig to 2000 psig. More preferred is a hydrogen gas pressure of about 1000 psig to 1500 psig.

The mixture in the presence of hydrogen gas, is contacted with a hydrogenolysis catalyst. The hydrogenolysis catalyst can be a homogeneous hydrogenolysis catalyst, for example, organometallic nickel compounds, complexed nickel salts, organometallic palladium compounds, complexed palladium salts, organometallic platinum compounds, and complexed platinum salts. Preferred are complexed nickel and complexed palladium salts consisting of the complex addition compound formed between two moles of a trialkyl triaryl, dialkylaryl, or an alkyldiarylphosphine. Preferred is when the nickel salt is nickel(II) chloride and the palladium salt is palladium(II) chloride.

The hydrogenolysis catalyst can be a heterogeneous hydrogenolysis catalyst for example, nickel, inorganic nickel compounds, palladium, inorganic palladium compounds, platinum, and inorganic platinum compounds. The heterogeneous hydrogenolysis catalyst can be supported nickel palladium, or platinum. The supported metal can be present on the support at about 0.1 to 70 weight percent of the combined metal and support weight. Preferred is when the supported metal is about five to 50 weight percent of the combined metal and support weight. The support can be for example, silica carbon, alumina, or diatomaceous earth. A preferred support material is kieselguhr. A preferred heterogeneous catalyst is nickel supported on kieselguhr.

An effective concentration of the hydrogenolysis catalyst is that typically recognized as effective to facilitate scission and hydrogenation of the silicon atoms of polysilanes. The concentration of hydrogenolysis catalyst required to be effective will depend upon such factors as the specific catalyst, the composition of the high-boiling residue, and the temperature and pressure at which the process is conducted. In general an effective concentration of the hydrogenolysis catalyst is considered to be within the range of about 0.1 to 30 weight percent of the combined weight of the high-boiling residue, organotrihalosilane, and catalysts. Preferred is when the hydrogenolysis catalyst is present within the range of about 1.0 to 10.0 weight percent. When the catalyst is supported, catalyst concentration should be based on the catalytic metal present.

A redistribution catalyst is employed in the present process at a concentration effective to facilitate redistribution of R. H. and X between different silicon atoms. The redistribution catalyst can be any catalyst effective in facilitating the exchange of R, H, and X between different silicon atoms. The redistribution catalyst can be homogeneous redistribution catalysts, for example, quaternary phosphonium halides quaternary ammonium halides, aluminum halides and boron halides. The redistribution catalyst can be heterogeneous redistribution catalysts, for example, alumina, aluminosilicates, acid exchanged zeolites, acid activated clays, and quaternized ion exchange resins containing quaternary ammonium halides or phosphonium halides. A preferred redistribution catalyst is gamma alumina. $Al_2O_3$.

In general, an effective concentration of the redistribution catalyst is considered to be within a range of about 0.1 to 30 weight percent of the combined weights of the high-boiling residue, organotrihalosilane, and catalysts. Preferred is when the redistribution catalyst is present within a range of about 1.0 to 10.0 weight percent.

The hydrogenolysis catalyst and redistribution catalyst can be added to the process as a single heterogeneous catalyst where one catalyst serves as a support for the other, for example, palladium metal supported on alumina.

The present process can be conducted at a temperature of about 100° C. to 400° C. Preferred is when the process is conducted at a temperature of about 300° C. to 350° C.

Organosilanes as described by Formula (3) are recovered from the present process. The organosilanes can be separated by standard methods for separating liquid mixtures, for example, distillation. The organosilanes can contain one, two, three, or four substituents R where R is as previously described. The organosilanes can contain zero, one, or two hydrogens substituted on each silicon atom. The organosilanes can contain zero, one, or two halogens substituted on each silicon atom. A preferred organosilane is selected from a group consisting of dimethyldichlorosilane and methyldichlorosilane.

The following examples are provided to illustrate the present invention. These examples are not intended to limit the claims presented herein.

EXAMPLE 1

The process was conducted in a stirred pressure vessel. The pressure vessel was flushed with dry nitrogen gas, then loaded with the catalyst or catalyst mixture, and the head of the pressure vessel attached with nitrogen flowing through the reactor. The catalysts tested and the weights of catalysts added to the process are presented in Table 2. The palladium on carbon catalyst (Pd/C). a hydrogenolysis catalyst, consisted of 1.5 weight percent palladium on carbon and was obtained from DeGussa, S. Plainfield, N.J. The redistribution catalyst consisted of alumina ($Al_2O_3$) purchased from Harshaw Filtrol, Elyria. Ohio. A combination hydrogenolysis and redistribution catalyst ($Pd/Al_2O_3$). obtained from Degussa, S. Plainfield. N.J., was also tested. The material CuCl was also tested in some runs as a potential catalyst.

About 24 g of high boiling residue from a direct process for the preparation of methylchlorosilanes by the reaction of methylchloride with silicon metalloid was added to the reactor through a port. The high-boiling residue was the fraction remaining in the bottom of a still after distilling off the monosilane fraction. The high-boiling residue was further strip distilled to separate it from solids. In some instances, up to 0.2 g of the catalyst used in the direct process (a mixture of CuCl, brass, tin, and copper phosphide) was present in the present process. The presence of the direct process catalyst at this concentration was considered to have no effect on the process. A typical composition for major components of the strip distilled high-boiling residue is presented in Table 1.

TABLE 1

| Composition of High-Boiling Residue | |
|---|---|
| Component | Weight % |
| $Me_3SiSiCl_2Me$ | 0.28 |
| $Me_2ClSiSiMe_2Cl$ | 4.05 |
| $Me_2ClSiSiMeCl_2$ | 20.88 |
| $MeCl_2SiSiMeCl_2$ | 34.71 |
| $Me_2ClSiCH_2SiMe_2Cl$ | 0.50 |
| $Me_2ClSiCH_2SiMeCl_2$ | 2.08 |
| $MeCl_2SiCH_2SiMeCl_2$ | 2.41 |
| Unidentified High Boilers | 25.27 |
| Solids | 6.67 |

Where indicated in Table 2, methyltrichlorosilane was introduced into the pressure vessel through a port. The pressure vessel was then pressurized with hydrogen gas to a pressure of about 450 psig to 500 psig, stirring commenced, and the contents heated to about 324° C., causing the pressure to increase to about 1000 psig to 1200 psig. The content of the reactor was heated at about 324° C. for about 16 hours. After the desired run time had elapsed, the content of the reactor was cooled and collected for analysis by gas chromatography (GC) using a thermal conductivity detector (TC).

The results are presented in Table 2. The percent disappearance of all the compounds initially present in the high-boiling residue is given as "HBR-conver. (%)." The percent conversion of $Me_2ClSiSiClMe_2$, $Me_2ClSiSiCl_2Me$, and $MeCl_2SiSiCl_2Me$ is presented in the row labelled "Disilane-Conv." The percent increase in Si—H containing species in the product labelled "HSi," is reported as the mole ratio of Si—H bonds formed in the reaction to the moles of Si present in the reaction times 100. The percent consumption of $MeSiCl_3$ (% $MeSiCl_3$ Consumed) is calculated as, (($MeSiCl_3$ Added—$MeSiCl_3$ in product)/$MeSiCl_3$ Added)×100. The "Net Product Distribution" is derived from the gross product distribution by subtracting out the levels of the components present in the feed stream and normalizing the distribution to 100 percent.

TABLE 2

| | Methyltrichlorosilane Depletion | | | | | | | | |
|---|---|---|---|---|---|---|---|---|---|
| | Run No. | | | | | | | | |
| | 32 | 15 | | 16 | | 17 | | 18 | |
| Catalyst(s) (g) | — | 1.5 | Pd/C | 3.0 | Pd/C | 3.0 | Pd/C | 3.0 | Pd/Al$_2$O$_3$ |
| | — | — | | 2.0 | CuCl | 2.0 | CuCl | 2.0 | CuCl |
| | — | — | | — | | 4.0 | Al$_2$O$_3$ | — | |
| MeSiCl$_3$ Added (g) | 18.2 | 0.0 | | 16.1 | | 24.7 | | 24.3 | |
| HBR Conv. (%) | 68.6 | 65.4 | | 72.8 | | 72.5 | | 78.9 | |
| Disilane Conv. (%) | 71.7 | 70.9 | | 97.9 | | 99.8 | | 100.0 | |
| % MeSiCl$_3$ Consumed | (10.8)* | — | | (26.1) | | 2.4 | | 9.9 | |
| HSi (%) | 28.7 | 33.1 | | 24.1 | | 7.4 | | 17.0 | |
| Net Product Distribution (Wt. %) | | | | | | | | | |
| MeH$_2$SiCl | 9.5 | 4.3 | | 1.7 | | 0.2 | | 1.2 | |
| HSiCl$_3$ | 0.5 | 0.6 | | 0.0 | | 2.4 | | 2.7 | |
| Me$_2$HSiCl | 10.6 | 9.6 | | 9.6 | | 1.1 | | 2.3 | |
| MeHSiCl$_2$ | 35.5 | 34.7 | | 41.1 | | 17.5 | | 32.0 | |
| SiCl$_4$ | 0.0 | 0.0 | | 0.0 | | 1.7 | | 0.8 | |
| Me$_3$SiCl | 1.4 | 1.2 | | 1.3 | | 1.1 | | 0.9 | |
| MeSiCl$_3$ | 14.3 | 22.3 | | 17.3 | | 0.0 | | 0.0 | |
| Me$_2$SiCl$_2$ | 25.5 | 27.2 | | 29.0 | | 76.1 | | 60.2 | |

*Bracketed values indicate an increase in methyltrichlorosilane.

The results indicate that there is no net consumption of MeSiCl$_3$ in the absence of a redistribution catalyst and that CuCl is not an effective catalyst in the process. Alumina is an effective redistribution catalyst in the process when either added separately or as a carrier for the hydrogenolysis catalyst.

EXAMPLE 2

The effect of time on methyltrichlorosilane consumption was evaluated in a process similar to that described in Example 1. The results are presented in Table 3. The headings for Table 3 are as described in Example 1.

TABLE 3

Effects of Time on Methyltrichlorosilane Consumption

| | Run No. | |
|---|---|---|
| | 18 | 19 |
| Time (h) | 16 | 1.5 |
| Catalyst(s) (g) | 3.0 Pd/Al$_2$O$_3$ | 3.0 Pd/Al$_2$O$_3$ |
| | 2.0 CuCl | 2.0 CuCl |
| MeSiCl$_3$ Added (g) | 24.3 | 24.0 |
| HBR Conv. (%) | 78.9 | 66.4 |
| Disilane Conv. (%) | 100.0 | 87.7 |
| % MeSiCl$_3$ Consumed | 9.9 | (3.3) |
| HSi (%) | 17.0 | 10.5 |
| Net Product Distribution (Wt. %) | | |
| MeH$_2$SiCl | 1.2 | 0.6 |
| HSiCl$_3$ | 2.7 | 0.5 |
| Me$_2$HSiCl | 2.3 | 1.4 |
| MeHSiCl$_2$ | 32.0 | 35.0 |
| SiCl$_4$ | 0.8 | 0.4 |
| Me$_3$SiCl | 0.9 | 2.8 |
| MeSiCl$_3$ | 0.0 | 5.1 |
| Me$_2$SiCl$_2$ | 60.2 | 54.3 |

EXAMPLE 3

A number of runs were made to evaluate the effects of pre-treatment of the high-boiling residue on methyltrichlorosilane consumption and the formation of silicon-hydrogen bonds. Except for the pre-treatment the process was run similar to that described in Example 1. The high-boiling residue was not initially strip distilled to separate it from solids, but in runs 23 and 24 was treated as described below. For run number 23, the high-boiling residue was treated by passing it through a sintered metal filter and twice adsorbing with 1.0 g of carbon per 20 g of filtered high-boiling residue. For run number 24, the high-boiling residue was filtered as described for run number 23. For run number 25, the high-boiling residue was not treated. In runs 23 and 25, the amount of high-boiling residue added to the pressure vessel was about 34-39 g.

TABLE 4

Effect of Pre-Treatment of The High-Boiling Residue

| | Run No. | | |
|---|---|---|---|
| | 23 | 24 | 25 |
| Catalyst(s) (g) | 3.0 | 3.0 | 3.0 |
| | Pd/Al$_2$O$_3$ | Pd/Al$_2$O$_3$ | Pd/Al$_2$O$_3$ |
| MeSiCl$_3$ Added (g) | 24.1 | 24.7 | 27.2 |
| HBR Conv. (%) | 75.5 | 81.3 | 70.2 |
| Disilane Conv. (%) | 100.0 | 100.0 | 100.0 |
| % MeSiCl$_3$ Consumed | 14.5 | 7.3 | 4.0 |
| HSi (%) | 22.7 | 22.0 | 10.6 |
| Net Product Distribution (Wt. %) | | | |
| MeH$_2$SiCl | 2.1 | 1.6 | 0.7 |
| HSiCl$_3$ | 7.2 | 6.6 | 5.3 |
| Me$_2$HSiCl | 2.2 | 1.8 | 1.0 |
| MeHSiCl$_2$ | 31.1 | 29.4 | 20.7 |
| SiCl$_4$ | 1.7 | 2.1 | 2.9 |
| Me$_3$SiCl | 1.0 | 0.8 | 0.9 |
| MeSiCl$_3$ | 0.0 | 0.0 | 0.0 |
| Me$_2$SiCl$_2$ | 54.1 | 57.6 | 67.4 |

The results indicate that pre-treatment of the high boiling residue results in increased MeSiCl$_3$ consumption and formation of Si—H containing monomers.

Example 4. The effectiveness of the homogeneous hydrogenolysis catalyst, bis(tributylphosphine)nickel-(II)-dichloride, hereafter referred to as BTBNi, was evaluated in a process similar to that described in Example 1. For this series of runs, about 18 g of the high-boiling residue, as described in Example 1, was added to the pressure reactor and 1.0 g of BTBNi. In run number 40, 1.0 g of the homogeneous redistribution catalyst tetrabutylphosphonium chloride, TBPCl, was also evaluated. In runs 42 through 44, 7.45 g of alumina (Al$_2$O$_3$) was added to the reactor as a redistribution catalyst. Run 42b represents a continuation of run 42a at a higher temperature after taking a sample from the reactor. Product samples from each run were analyzed as described in Example 1 and the results are presented in Table 5. The headings for Table 5 are as described in Example 1.

TABLE 5

| | \multicolumn{6}{c}{BTBNi as Hydrogenolysis Catalysis} |
| | \multicolumn{6}{c}{Run No.} |
| | 37 | 40 | 42a | 42b | 43 | 44 |
|---|---|---|---|---|---|---|
| Temp. (°C.) | 135 | 135 | 135 | 325 | 325 | 325 |
| Press. (psig) | 505 | 505 | 505 | 1150 | 1150 | 1100 |
| Time (h) | 17 | 17 | 17 | 17 | 3 | 1 |
| Catalyst(s) | BTBNi | BTBNi | BTBNi | BTBNi | BTBNi | BTBNi |
| | — | TBPCl | $Al_2O_3$ | $Al_2O_3$ | $Al_2O_3$ | $Al_2O_3$ |
| $MeSiCl_3$ Added (g) | 18.3 | 18.4 | 18.5 | 18.5 | 18.6 | 18.2 |
| HBR Conv. (%) | 87.9 | 82.9 | 76.4 | 89.2 | 86.7 | 86.0 |
| Disilane Conv. (%) | 93.7 | 98.5 | 82.1 | 99.8 | 95.0 | 94.1 |
| % $MeSiCl_3$ Consumed | (2.6) | 10.3 | (21.7) | 39.0 | 30.3 | 15.4 |
| HSi (%) | 42.9 | 36.6 | 35.5 | 36.1 | 41.5 | 39.9 |
| Net Product Distribution (Wt. %) | | | | | | |
| $MeH_2SiCl$ | 8.1 | 2.1 | 2.3 | 4.8 | 5.7 | 6.9 |
| $HSiCl_3$ | 0.1 | 0.6 | 0.0 | 2.2 | 0.2 | 0.1 |
| $Me_2HSiCl$ | 0.9 | 1.1 | 6.7 | 3.5 | 3.0 | 4.0 |
| $MeHSiCl_2$ | 63.6 | 59.1 | 61.4 | 48.6 | 63.9 | 62.1 |
| $SiCl_4$ | 0.0 | 0.0 | 0.0 | 0.0 | 0.0 | 0.0 |
| $Me_3SiCl$ | 1.2 | 1.2 | 0.7 | 1.0 | 1.8 | 1.4 |
| $MeSiCl_3$ | 2.5 | 0.0 | 20.5 | 0.0 | 0.0 | 0.0 |
| $Me_2SiCl_2$ | 23.5 | 35.7 | 8.0 | 37.7 | 25.0 | 25.1 |

The results demonstrate the effectiveness of the homogeneous hydrogenolysis catalyst BTBNi, when combined with the redistribution catalyst TBPCl or $Al_2O_3$, in converting disilanes to monosilanes while consuming $MeSiCl_3$.

Example 5. The effectiveness of a heterogeneous catalyst comprising nickel supported on kieselguhr was evaluated in a process similar to that described in Example 1. For this series of runs, 25 g to 28 g of the high-boiling residue, as described in Example 1, was added to the pressure reactor along with 2.0 g of a catalyst comprising 55 weight percent nickel on kieselguhr (Ni/Kgr) obtained from United Catalyst, Louisville, Ky. For runs 57 through 59, 7.5 g of alumina, as previously described, was added to the process as a redistribution catalyst. The catalyst used in run 55 was reused in run 56. The catalysts used in run 57 were pretreated by contacting with hydrogen gas at a pressure of about 1200 psi, at 325° C., for one hour. The catalysts used in run 57 were reused in runs 58 and 59. The process was run at a temperature of about 325° C. and a pressure of about 1300 psig.

Product samples from each run were analyzed as described in Example 1 and the results are presented in Table 6. The headings for Table 6 are as previously described.

TABLE 6

| | \multicolumn{5}{c}{Effectiveness of Nickel Supported on Kieselguhr as Hydrogenolysis Catalyst} |
| | \multicolumn{5}{c}{Run No.} |
| | 55 | 56 | 57 | 58 | 59 |
|---|---|---|---|---|---|
| Catalyst(s) | Ni/Kgr | Ni/Kgr | Ni/Kgr | Ni/Kgr | Ni/Kgr |
| | — | — | $Al_2O_3$ | $Al_2O_3$ | $Al_2O_3$ |
| $MeSiCl_3$ Added (g) | 19.3 | 17.5 | 18.4 | 18.4 | 19.8 |
| HBR Conv. (%) | 61.0 | 75.5 | 90.4 | 88.6 | 88.2 |
| Disilane Conv. (%) | 58.6 | 75.9 | 99.6 | 100.0 | 99.9 |
| % $MeSiCl_3$ Consumed | (11.2) | 11.8 | 5.5 | 35.1 | 32.7 |
| HSi (%) | 7.8 | 23.2 | 16.9 | 32.9 | 42.2 |
| Net Product Distribution (Wt. %) | | | | | |
| $MeH_2SiCl$ | 0.0 | 1.9 | 0.8 | 3.0 | 5.0 |
| $HSiCl_3$ | 2.6 | 0.7 | 3.7 | 2.3 | 2.8 |
| $Me_2HSiCl$ | 3.9 | 8.0 | 1.5 | 3.3 | 3.3 |
| $MeHSiCl_2$ | 31.1 | 56.1 | 34.8 | 47.6 | 50.7 |
| $SiCl_4$ | 3.8 | 0.0 | 1.3 | 0.0 | 0.0 |
| $Me_3SiCl$ | 1.4 | 1.4 | 0.7 | 0.9 | 0.7 |
| $MeSiCl_3$ | 28.5 | 0.0 | 0.0 | 0.0 | 0.0 |
| $Me_2SiCl_2$ | 28.7 | 31.9 | 57.4 | 42.9 | 37.4 |

The data presented in Table 6 indicate that nickel supported on kieselguhr when reused in the process can effect the consumption of added methyltrichlorosilane. However, the consumption of added methyltrichlorosilane is significantly increased when the nickel on kieselguhr catalyst is employed in the presence of a redistribution catalyst such as alumina.

We claim:

1. A process for converting polysilanes to organosilanes, the process comprising:

(A) forming a mixture comprising polysilanes of formula $$R_aH_bSi_nX_{2n+2-a-b}$$

and an organotrihalosilane of formula $$RSiX_3$$

(B) contacting the mixture with hydrogen gas at a pressure of 50 psig to 10,000 psig, a hydrogenolysis catalyst, and a redistribution catalyst, at a temperature of 100° C. to 400° C. and (C) recovering organohalosilanes of formula $$R_cH_dSiX_{4-c-d}$$

where each R is a radical independently selected from a group consisting of alkyls of one to six carbon atoms, aryls, alkoxys of one to six carbon atoms, trimethylsilyl, and trifluoropropyl. X is a halogen $n=2$ to 20, $a=0$ to $2n+2$, $b=0$ to $2n+2$, $a+b=0$ to $2n+2$, $c=1, 2, 3,$ or $4$, $d=0, 1,$ or $2$, and $c+d=2, 3,$ or $4$.

2. A Process according to claim 1, where n is two.

3. A Process according to claim 1, where $a=(2n+2)/2$ to $2n+2$.

4. A Process according to claim 1, where R is methyl.

5. A process according to claim 1, where X is chlorine.

6. A process according to claim 1, where the polysilanes are disilanes.

7. A Process according to claim 1, where the organotrihalosilane is methyltrichlorosilane.

8. A Process according to claim 1, where the organotrihalosilane is about 30 to 50 weight percent of the mixture.

9. A Process according to claim 1, where the hydrogen gas is at a pressure of about 1000 psig to 1500 psig.

10. A Process according to claim 1, where the hydrogenolysis catalyst is selected from a group consisting of organometallic nickel compounds, complexed nickel salts, organometallic palladium compounds complexed palladium salts, organometallic platinum compounds, and complexed platinum salts.

11. A Process according to claim 1, where the hydrogenolysis catalyst is selected from a group consisting of complexed nickel and complexed palladium salts consisting of the complex addition compound formed between two moles of a trialkyl, triaryl, dialkylaryl, or an alkyldiarylphosphine.

12. A Process according to claim 1, where the hydrogenolysis catalyst is bis(tributylphosphine)nickel(II)dichloride.

13. A Process according to claim 1, where the hydrogenolysis catalysis is selected from a group consisting of nickel, inorganic nickel compounds, palladium, inorganic palladium compounds, platinum, and inorganic platinum compounds.

14. A process according to claim 1, where the hydrogenolysis catalyst is selected from a group consisting of supported nickel, supported palladium, and supported platinum.

15. A process according to claim 14, where the support is selected from a group consisting of silica, carbon, alumina, and diatomaceous earth.

16. A process according to claim 15, where the hydrogenolysis catalyst is nickel supported on kieselguhr.

17. A process according to claim 1, where the hydrogenolysis catalyst is present at a concentration within a range of about 1.0 to 10.0 weight percent of the combined weight of the high-boiling residue, organotrihalosilane, and catalysts.

18. A process according to claim 1, where the redistribution catalyst is selected from a group consisting of quaternary phosphonium halides, quaternary ammonium halides, aluminum halides, and boron halides.

19. A process according to claim 1, where the redistribution catalyst is selected from a group consisting of alumina aluminosilicates, acid-exchange zeolites, acid activated clays, and quaternized ion exchange resins containing quaternary ammonium halides or phosphonium halides.

20. A process according to claim 19, where the redistribution catalyst is alumina.

21. A process according to claim 1, where the redistribution catalyst is present within a range of about 1.0 to 10.0 weight percent of the combined weights of the high-boiling residue, organotrihalosilane, and catalysts.

22. A process according to claim 1, where the hydrogenolysis catalyst and the redistribution catalyst are added to the process as a single heterogeneous catalyst where one catalyst serves as a support for the other.

23. A process according to claim 22, where palladium metal is supported on alumina.

24. A process according to claim 1, where the temperature is within a range of about 300° C. to 350° C.

25. A process according to claim 1, where the organosilane is selected from a group consisting of dimethyldichlorosilane and methyldichlorosilane.

26. A process according to claim 1, where the polysilane is dimethyltetrachlorodisilane.

27. A process according to claim 1, where R is methyl, n=2, X is chlorine, the hydrogen gas pressure is at a pressure of about 1000 psig to 1500 psig the temperature is within a range of about 300° C. to 350° C., the hydrogenolysis catalyst is selected from a group consisting of bis(tributylphosphine)nickel(II)-dichloride, palladium supported on carbon, and nickel supported on kieselguhr, and the redistribution catalyst is alumina.

* * * * *